United States Patent
Pedragosa-Moreau et al.

(10) Patent No.: US 9,045,788 B2
(45) Date of Patent: Jun. 2, 2015

(54) PROCESS FOR THE ENZYMATIC SYNTHESIS OF (7S)-1-(3,4-DIMETHOXYBICYCLO[4.2.0]OCTA-1,3,5-TRIEN-7-YL) N-METHYL METHANAMINE, AND APPLICATION IN THE SYNTHESIS OF IVABRADINE AND SALTS THEREOF

(71) Applicant: LES LABORATOIRES SERVIER, Suresnes Cedex (FR)

(72) Inventors: Sandrine Pedragosa-Moreau, Orleans (FR); François Lefoulon, Orleans (FR); Francisco Moris Varas, Gijon (ES); Javier Gonzalez Sabin, Oviedo (ES)

(73) Assignee: LES LABORATOIRES SERVIER, Suresnes Cedex (FR)

( * ) Notice: Subject to any disclaimer, the term of this patent is extended or adjusted under 35 U.S.C. 154(b) by 51 days.

(21) Appl. No.: 13/941,990

(22) Filed: Jul. 15, 2013

(65) Prior Publication Data

US 2014/0024088 A1 Jan. 23, 2014

(30) Foreign Application Priority Data

Jul. 17, 2012 (FR) ..................... 12 56913

(51) Int. Cl.
| | | |
|---|---|---|
| *C12P 41/00* | (2006.01) | |
| *C12P 17/10* | (2006.01) | |
| *C07C 269/04* | (2006.01) | |
| *C07D 223/16* | (2006.01) | |
| *C12P 13/02* | (2006.01) | |

(52) U.S. Cl.
CPC ............... *C12P 17/10* (2013.01); *C07C 269/04* (2013.01); *C07D 223/16* (2013.01); *C12P 41/008* (2013.01); *C12Y 301/01003* (2013.01); *C12P 13/02* (2013.01)

(58) Field of Classification Search
None
See application file for complete search history.

(56) References Cited

U.S. PATENT DOCUMENTS

| | | |
|---|---|---|
| 6,982,350 B2 | 1/2006 | Lerestif et al. |
| 7,064,200 B2 * | 6/2006 | Lerestif et al. ................ 540/523 |

FOREIGN PATENT DOCUMENTS

| | | |
|---|---|---|
| EP | 1 598 333 | 11/2005 |
| EP | 1598333 A1 * | 11/2005 |
| EP | 2 495 237 | 9/2012 |
| WO | 2010/072409 | 7/2010 |

OTHER PUBLICATIONS

Lavandera, I., Fernandez, S., Ferrero, M., and Gotor, V. "First Regioselective Enzymatic Alkoxycarbonylation of Primary Amines. Synthesis of Novel 5'- and 3'-Carbamates of Pyrimidine 3',5'-Diaminonucleoside Derivatives Including BVDU Analogues", J. Org. Chem 2004, vol. 69, pp. 1748-1751.*
Bodis, J., Lefferts, L., Muller, T.E., Pestman, R., and Lercher, J.A. "Activity and selectivity control in reductive amination of butyraldehyde over noble metal catalysts", Catalysis Letters 2005, vol. 104, pp. 23-28.*
French Preliminary Search Report for FR1256913 of Mar. 11, 2013.
Orsat, B. et al., Journal of the American Chemical Society, vol. 118, No. 3, p. 712-713, Jan. 1, 1996.

* cited by examiner

*Primary Examiner* — Allison Fox
*Assistant Examiner* — Michelle F Paguio Frising
(74) *Attorney, Agent, or Firm* — Hueschen and Sage

(57) ABSTRACT

Process for the enzymatic synthesis of the compound of formula (I), (7S)-1-(3,4-dimethoxybicyclo[4.2.0]octa-1,3,5-trien-7-yl)N-methyl methanamine:

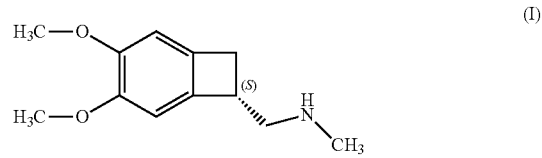

(I)

and application in the synthesis of ivabradine and addition salts thereof with a pharmaceutically acceptable acid.

12 Claims, No Drawings

PROCESS FOR THE ENZYMATIC SYNTHESIS OF (7S)-1-(3,4-DIMETHOXYBICYCLO[4.2.0]OCTA-1,3,5-TRIEN-7-YL) N-METHYL METHANAMINE, AND APPLICATION IN THE SYNTHESIS OF IVABRADINE AND SALTS THEREOF

The present invention relates to a process for the enzymatic synthesis of the compound of formula (I), (7S)-1-(3,4-dimethoxybicyclo[4.2.0]octa-1,3,5-trien-7-yl)N-methyl methanamine:

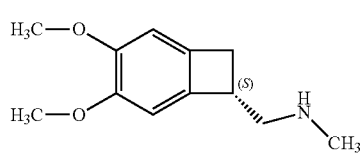
(I)

and to the application thereof in the synthesis of ivabradine of formula (II):

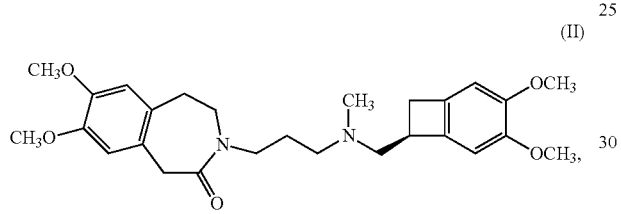
(II)

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one,
its addition salts with a pharmaceutically acceptable acid and their hydrates.

Ivabradine, and addition salts thereof with a pharmaceutically acceptable acid, and more especially the hydrochloride thereof, have very valuable pharmacological and therapeutic properties, especially bradycardic properties, which render those compounds useful in the treatment or prevention of various clinical conditions of myocardial ischaemia, such as angina pectoris, myocardial infarction and associated rhythm disorders, as well as in various pathologies involving rhythm disorders, especially supraventricular rhythm disorders, and in heart failure.

The preparation and therapeutic use of ivabradine and addition salts thereof with a pharmaceutically acceptable acid, and more especially the hydrochloride thereof, have been described in European patent specification EP 0 534 859.

That patent specification describes the synthesis of ivabradine hydrochloride starting from the compound of formula (I).

The compound of formula (I) is a key intermediate in the synthesis of ivabradine and its pharmaceutically acceptable salts.

The prior art discloses several methods for obtaining the compound of formula (I).

Patent specification EP 0 534 859 describes the synthesis of the compound of formula (I) by reduction of the racemic nitrile of formula (III):

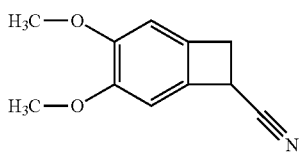
(III)

by $BH_3$ in tetrahydrofuran,
followed by addition of hydrochloric acid, to yield the hydrochloride of the racemic amine of formula (IV):

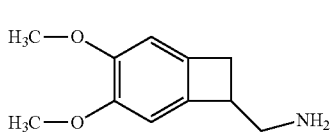
(IV)

which is reacted with ethyl chloroformate to yield the carbamate of formula (V):

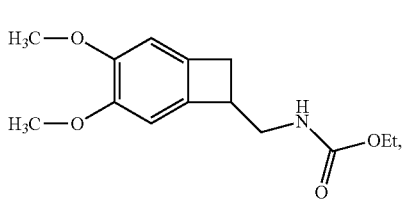
(V)

the reduction of which, by $LiAlH_4$, yields the racemic methylated amine of formula (VI):

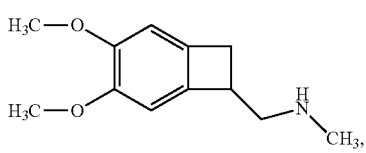
(VI)

the resolution of which, using camphorsulphonic acid, yields the compound of formula (I).

That method has the disadvantage of yielding the compound of formula (I) in only a very low yield of 2 to 3% starting from the racemic nitrile of formula (III).

That very low yield is due to the low yield (4 to 5%) of the step of resolution of the secondary amine of formula (VI).

Patent specification EP 1 598 333 describes obtaining the compound of formula (I) by conversion of the racemic primary amine of formula (IV) into a salt using N-acetyl-L-glutamic acid, followed by recrystallisation and then returning to the base, to yield the optically active primary amine of formula (VII):

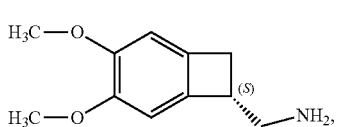
(VII)

which is then methylated using the same reaction sequence as above (conversion into the carbamate, and then reduction).

That method results in the methanamine of formula (I) in 4 steps in a yield of about 30% starting from the racemic primary amine of formula (IV).

The problem of the present invention was to obtain the compound of formula (I) by reducing the number of steps starting from the racemic primary amine of formula (IV) whilst maintaining a good overall yield.

More specifically, the present invention relates to a process for the synthesis of the carbamate of formula (IX):

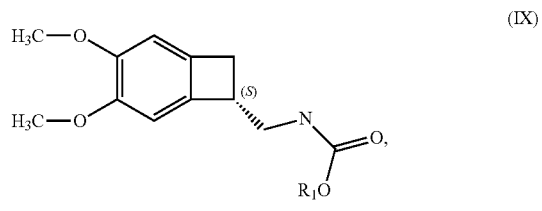

wherein $R_1$ represents a linear or branched $C_1$-$C_6$alkyl, allyl or benzyl group, by enantioselective enzymatic acylation of the racemic amine of formula (IV) using a lipase (EC 3.1.1.3 in the international classification of enzymes)

with a carbonate of formula $R_1O$—(CO)—$OR_1$, wherein $R_1$ is as defined hereinbefore, in an amount ranging from 1 to 15 molar equivalents relative to the amine of formula (IV), in an organic or aqueous solvent, a mixture of organic solvents or a mixture of organic and aqueous solvents, at a concentration from 5 to 500 g/L of compound of formula (IV) per liter of solvent or mixture of solvents, at an E/S ratio of from 10/1 to 1/100, preferably from 1/1 to 1/10, at a temperature from 25° C. to 40° C.

The carbamate of formula (IX) obtained by the process of the present invention preferably has an enantiomeric purity of more than 85%, that is to say an enantiomeric excess of more than 70%.

Among the lipases which may be used in the enzymatic esterification process according to the present invention there may mentioned, without implying any limitation, the lipases of *Pseudomonas fluorescens*, of *Pseudomonas cepacia*, of porcine pancreas, and the lipases PS 'Amano' SD (*Burkholderia cepacia*) and IM (immobilised on Diatomite).

Lipases that are preferred according to the invention are the lipases of *Pseudomonas cepacia* and PS 'Amano' IM.

Preferred carbonates $R_1O$—(CO)—$OR_1$ are those wherein $R_1$ represents an allyl, ethyl or benzyl group.

Among the organic solvents that may be used for the enzymatic acylation reaction according to the present invention, there may be mentioned, without implying any limitation, ethyl acetate, TBME, THF, 2-MeTHF, toluene, 1,4-dioxane, tert-amyl alcohol, CPME and acetonitrile.

Preferred solvents are TBME, THF, 2-MeTHF and 1,4-dioxane, on their own or in admixture with a buffer of pH=7.

The enzymatic acylation scheme according to the invention is as follows:

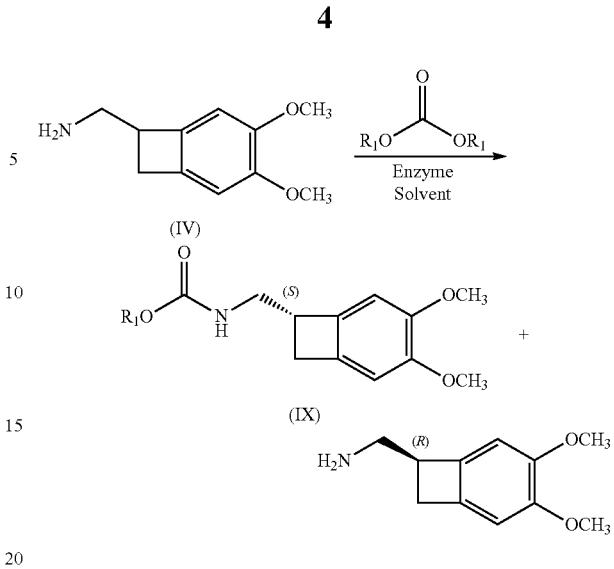

The carbamate of formula (IX) is then isolated from the reaction mixture, and then it is reduced using an aluminium hydride such as lithium aluminium hydride (LiAlH$_4$) or sodium bis(2-methoxyethoxy)aluminium hydride (Red-Al) to yield the methylated amine of formula (I).

The latter is subsequently either coupled with a compound of formula (X):

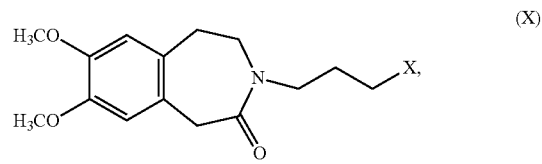

wherein X represents a halogen atom, preferably an iodine atom, or, in the presence of a reducing agent, subjected to a reductive amination reaction with a compound of formula (XI):

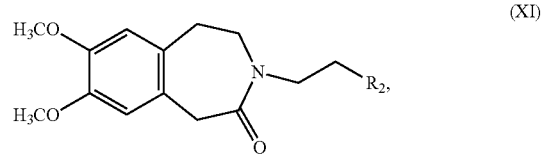

wherein $R_2$ represents a group selected from CHO and CHR$_3$R$_4$, wherein $R_3$ and $R_4$ each represent a linear or branched (C$_1$-C$_6$)alkoxy group or form, together with the carbon atom carrying them, a 1,3-dioxane, 1,3-dioxolane or 1,3-dioxepane ring, to yield ivabradine, which is then converted into an addition salt with a pharmaceutically acceptable acid.

The compound of formula (I) may also be used in the reductive amination reaction in the form of its addition salt with a pharmaceutically acceptable acid, preferably its hydrochloride. In that case, ivabradine is obtained directly in the form of the hydrochloride.

DEFINITIONS

A racemic compound is understood to be a compound in the form of a mixture of two enantiomers in a ratio of from 55:45 to 45:55.

Enantioselective acylation of an amine in the form of a mixture of two enantiomers is understood to be preferential acylation of one of the enantiomers of the mixture.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid.

Among the reducing agents that may be used for the reductive amination reaction between the compound of formula (I) and the compound of formula (XI) there may be mentioned, without implying any limitation, hydride donor compounds such as sodium triacetoxyborohydride or sodium cyanoborohydride, and dihydrogen in the presence of a catalyst such as palladium, platinum, nickel, ruthenium, rhodium, or a compound thereof, especially on a support or in the form of oxides.

The preferred reducing agent for the reductive amination reaction between the compound of formula (I) and the compound of formula (XI) is dihydrogen catalysed by palladium-on-carbon.

The Examples hereinbelow illustrate the invention.

ABBREVIATIONS

CPME CycloPentyl Methyl Ether
DEA DiEthylAmine
E Enantioselectivity coefficient
E/S Enzyme/Substrate ratio expressed in g/g
ee enantiomeric excess
eq molar equivalent
HPLC High Performance Liquid Chromatography
Red-Al sodium bis(2-methoxyethoxy)aluminium hydride
NMR Nuclear Magnetic Resonance (spectroscopy)
TBME Tert-Butyl Methyl Ether
THF TetraHydroFuran
2-Me HF 2-MethylTetraHydroFuran
rpm revolutions per minute

Example 1

Ethyl{[(7S)-3,4-dimethoxybicyclo[4.2.0]octa-1,3,5-trien-7-yl]methyl}-carbamate 5 mg of 1-(3,4-dimethoxybicyclo[4.2.0]octa-1,3,5-trien-7-yl)methanamine and 12.6 mg (10 eq) of diethyl carbonate are dissolved in 2-MeTHF.

5 mg of lipase II of *Pseudomonas cepacia* (PS-CII Amano) are then added to the mixture (E/S ratio 1/1). The reaction mixture is maintained at 30° C., with rotary stirring at 250 rpm, for 24 hours to 96 hours.

The reaction is monitored by chiral-phase HPLC under conditions allowing the enantiomeric excesses of both the carbamate and the amine to be determined:
Chiral-phase conditions: Chiralpak® IC 250*4.6 column
50% absolute ethanol+0.1% DEA+50 heptane+0.1% DEA
1 ml/min, 25° C., 288 nm

| Concentration | t | Conversion c (%) | Ee (%) amine (R) | Ee (%) carbamate (S) | E |
|---|---|---|---|---|---|
| 10 g/L | 24 hrs | 38 | 57.7 | 92.3 | 45 |
| 20 g/L | 96 hrs | 51 | 93.2 | 88.8 | 58 |
| 50 g/L | 96 hrs | 57 | 99.9 | 76.1 | 69 |

Example 2

Ethyl{[(7S)-3,4-dimethoxybicyclo[4.2.0]octa-1,3,5-trien-7-yl]methyl}-carbamate 0.5 g of 1-(3,4-dimethoxybicyclo[4.2.0]octa-1,3,5-trien-7-yl)methanamine is dissolved in 50 mL of 2-MeTHF and then diethyl carbonate (1.5 mL, 12 eq) is added. 0.5 g (E/S ratio 1/1) of lipase II of *Pseudomonas cepacia* (PS-CII Amano) is added to the mixture, which is maintained at 30° C. for 48 hours with stirring at 220 rpm.

After 48 hours, the reaction mixture is filtered in order to remove the enzyme and is then evaporated. The carbamate of configuration S is obtained after separation on an $SiO_2$ column, eluting with cyclohexane/ethyl acetate 95/5, then 80/20 and finally 50/50, to recover the more polar amine.

The ethyl carbamate of configuration S (224 mg) is then obtained in a yield of 32.5% relative to the starting amine (65% relative to the expected amount of carbamate) and with an enantiomeric purity of 90%.

The reaction is monitored by chiral-phase HPLC under conditions allowing the enantiomeric excesses of both the carbamate and the amine to be determined:
Chiral-phase conditions: Chiralpak® IC 250*4.6 column
50% absolute ethanol+0.1% DEA+50 heptane+0.1% DEA
1 ml/min, 25° C., 288 nm

| Time (h) | Conversion (%) | Ee (carbamate)(%) | Ee (amine) (%) | E |
|---|---|---|---|---|
| 24 | 34 | 88 | 45 | 23 |
| 48 | 53 | 81 | 93 | 35 |

Example 3

Allyl{[(7S)-3,4-dimethoxybicyclo[4.2.0]octa-1,3,5-trien-7-yl]methyl}-carbamate 0.87 g of 1-(3,4-dimethoxybicyclo[4.2.0]octa-1,3,5-trien-7-yl)methanamine are dissolved in 100 mL of 2-MeTHF and then diallyl carbonate (1.5 mL, ~2 eq) is added. 0.5 g (E/S ratio 1/1) of lipase II of *Pseudomonas cepacia* (PS-CII Amano) is then added to the mixture, which is maintained at 30° for 42 hours with stirring at 220 rpm.

The reaction mixture is then filtered in order to remove the enzyme and then evaporated. The allyl carbamate is obtained after separation on an $SiO_2$ column, eluting with cyclohexane/ethyl acetate 95/5, then 80/20 and finally 50/50, to recover the more polar amine. The allyl carbamate of configuration S (440 mg) is then obtained in a yield of 35% relative to the starting amine (70% relative to the expected amount of carbamate) and with an enantiomeric purity of 88%.

| Time (h) | Conversion (%) | Ee (carbamate)(%) | Ee (amine) (%) | E |
|---|---|---|---|---|
| 42 | 50 | 89 | 82 | 26 |

The reaction mixture is analysed by reverse-phase HPLC, and the enantioselectivity (ee) of the carbamate and of the amine are monitored by chiral-phase HPLC in accordance with the methods described hereinbelow:
Reverse-phase conditions: Phenomenex® LUNA HST 50*3 column C18(2) 2.5 μm
0% to 100% of B over 8 min 0.8 ml/min 40° C.
A (1000 water+25 ACN+1 TFA)
B (1000 ACN+25 water+1 TFA)
Chiral-phase conditions: Chiralpak® IC 250*4.6 column
50% isopropanol+0.1% EA+50 heptane+0.1% EA
1 ml/min, 30° C., 288 nm Example 4

Benzyl{[(7S)-3,4-dimethoxybicyclo[4.2.0]octa-1,3,5-trien-7-yl]methyl}-carbamate 0.5 g of 1-(3,4-dimethoxybicyclo[4.2.0]octa-1,3,5-trien-7-yl)methanamine are dissolved in 50 mL of 2-MeTHF, and then dibenzyl carbonate (4.5 g, 7 eq) is added. 0.5 g (E/S ratio 1/1) of lipase II of *Pseudomonas cepacia* (PS-C II Amano) is added to the mixture, which is maintained at 30° with stirring at 220 rpm.

After 24 hours, the reaction mixture is filtered to remove the enzyme and is then evaporated. The carbamate of configuration S is obtained after separation on an $SiO_2$ column, eluting with cyclohexane/ethyl acetate 95/5, then 80/20 and finally 50/50, to recover the more polar amine. The benzyl carbamate of configuration S (0.26 g) is then obtained in a yield of 30% relative to the starting amine (60% relative to the expected amount of carbamate) and with an enantiomeric purity of 95%.

The reaction mixture is analysed by reverse-phase HPLC, and the enantioselectivity (ee) of the carbamate and of the amine are monitored by chiral-phase HPLC in accordance with the methods described hereinbelow:
Reverse-phase conditions: Phenomenex® LUNA HST 50*3 column C18(2) 2.5 μm
0% to 100% of B over 8 min 0.8 ml/min 40° C.
A (1000 water+25 ACN+1 TFA)
B (1000 ACN+25 water+1 TFA)
Chiral-phase conditions: Chiralpak® IC 250*4.6 column
50% isopropanol+0.1% DEA+50 heptane+0.1% DEA
1 ml/min, 25° C., 288 nm

| Time (h) | Conversion (%) | Ee (carbamate)(%) | Ee (amine) (%) | E |
|---|---|---|---|---|
| 24 | 58 | 90 | 87 | 12 |

Example 5

(7S)-3,4-Dimethoxybicyclo[4.2.0]octa-1,3,5-trien-7-yl]N-methyl methanamine

Load into a reactor, under nitrogen, lithium aluminium hydride (1.41 kg) and tetrahydrofuran (32.5 l), and then pour in, at 20° C., a solution of ethyl{[(7S)-3,4-dimethoxybicyclo[4.2.0]octa-1,3,5-trien-7-yl]methyl}carbamate (5 kg) in tetrahydrofuran (50 l). Heat at reflux for 1 hour and then cool to a temperature below 15° C. and hydrolyse the reaction mixture with water (1 l), 5N aqueous sodium hydroxide solution (1 l) and then water (1 l). Filter off the solid obtained. Dry the organic phase. The title product is recovered in the form of an oil, in a yield of 93%.

$^1$H NMR (DMSO-d6, ppm/TMS)=2.60 (m; 3H); 2.85 (m; 1H); 3.15 (m; 1H); 3.25 (dd; 1H); 3.30 (m; 1H); 3.62 (m; 1H); 3.70 (s; 6H); 6.82 (s; 1H); 6.89 (s; 1H); 8.48 (sl; 1H).

Example 6

(7S)-3,4-Dimethoxybicyclo[4.2.0]octa-1,3,5-trien-7-yl]N-methyl methanamine hydrochloride Load (7S)-3,4-dimethoxybicyclo[4.2.0]octa-1,3,5-trien-7-yl]N-methyl methanamine (5 kg), ethyl acetate (40 l) and ethanol (10 l) into a reactor. Stir at 20° C. for 30 minutes and then add, via the bottom valve of the reactor or an immersed tube, gaseous hydrogen chloride (1.012 kg). The suspension obtained is stirred at 15-20° C. for 1 hour and then is filtered or is drained under suction. The precipitate is washed with a mixture of ethyl acetate/ethanol 4/1 (2×5 l) and is then dried to yield the title product in a yield of 92%.

Example 7

Ivabradine Hydrochloride

Load 5.5 kg of 3-[2-(1,3-dioxolan-2-yl)ethyl]-7,8-dimethoxy-1,3-dihydro-2H-3-benzazepin-2-one, 27.5 l of ethanol and 550 g of palladium-on-carbon into an autoclave.

Purge with nitrogen and then with hydrogen, heat to 55° C., and then hydrogenate at that temperature under a pressure of 5 bars until the theoretical amount of hydrogen has been absorbed.

Then return to ambient temperature and then depressurise the autoclave.

Then add 4 kg of (7S)-3,4-dimethoxybicyclo[4.2.0]octa-1,3,5-trien-7-yl]N-methyl methanamine hydrochloride, 11 l of ethanol, 5.5 l of water and 1 kg of palladium-on-carbon.

Purge with nitrogen and then with hydrogen, heat to 85° C., and then hydrogenate at that temperature under a pressure of 30 bars until the theoretical amount of hydrogen has been absorbed.

Then bring back to ambient temperature, purge the autoclave and then filter the reaction mixture; distil off the solvents and then isolate the ivabradine hydrochloride by crystallisation from a toluene/1-methyl-2-pyrrolidinone mixture.

Ivabradine hydrochloride is thereby obtained in a yield of 85% and with a chemical purity greater than 99%.

Example 8

Screening of lipases for the enzymatic acylation of 1-(3,4-dimethoxybicyclo[4.2.0]octa-1,3,5-trien-7-yl)methanamine Racemic 1-(3,4-dimethoxybicyclo[4.2.0]octa-1,3,5-trien-7-yl)methanamine (5 mg; c=10 g/L) and the carbonate of formula $R_1O$—(CO)—$OR_1$ (10 eq) are dissolved in 0.5 mL of TBME.

5 mg (c=10 g/L) of the lipase being studied are then added to the medium (E/S ratio=1/1).

The reaction mixture is maintained at 30° C., with rotary stirring at 250 rpm for 24 hours.

The reaction mixtures are analysed by chiral-phase HPLC for checking the enantioselectivity, in accordance with the method:
Chiralpak®IC 20 pm column, 250*4.6 acetonitrile/propan-2-ol/DEA 90/10/0.1%; 1.3 ml/min; 30° C., 288 nm The results are summarised in the following table:

| Lipase | Carbonate | Product | Conversion c (%) | ee (%) Amine (R) | ee (%) Carbamate (S) | E |
|---|---|---|---|---|---|---|
| *Pseudomonas cepacia* lipase II | 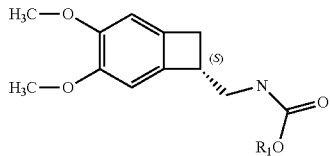 | IXa | 59 | >99.9 | 69.8 | 40 |
| *Pseudomonas fluorescens* | | | 14 | 12.3 | 73.8 | 7 |
| Lipase PS 'Amano' SD | | | 4 | 3.9 | 83.2 | 11 |
| Lipase PS 'Amano' IM | | | 52 | 91.6 | 83.5 | 36 |
| *Pseudomonas cepacia* lipase | 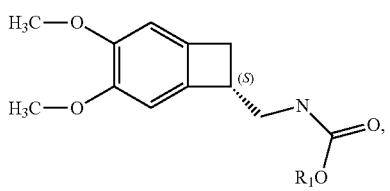 | IXb | 57 | 97.0 | 73.4 | 26 |
| *Pseudomonas fluorescens* | | | 5 | 3.9 | 78.2 | 8 |
| Lipase PS 'Amano' IM | | | 33 | 44.4 | 89.0 | 27 |
| *Pseudomonas cepacia* lipase II | 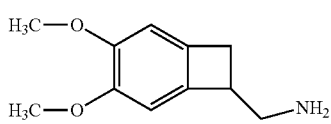 | IXc | 16 | 17.7 | 89.6 | 22 |
| *Pseudomonas fluorescens* | | | 3 | 2.2 | 66.1 | 5 |
| Lipase PS 'Amano' IM | | | 12 | 11.2 | 84.6 | 13 |

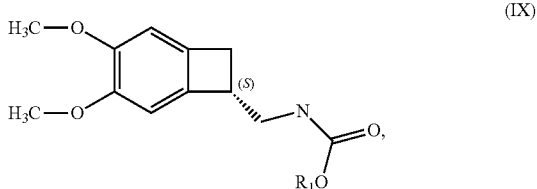

IXa: $R_1$ = allyl
IXb: $R_1$ = benzyl
IXc: $R_1$ = ethyl aEnantiomeric excess ee (en %) = % enantioE2 − % enantioE1/% enantio E2 + % enantio E1 (enantio E2 being the predominant enantiomer)
bEnantioselectivity coefficient E = ln[(1 − c)(1 − ee(S)]/ln[(1 − c)(1 + ee(S)];
c = level of conversion = ee(amine)/[ee(carbamate) + ee(amine)]

The invention claimed is:

1. A process for the synthesis of a compound of formula (IX):

![Formula IX]

wherein $R_1$ represents a linear or branched $C_1$-$C_6$alkyl, allyl or benzyl group,
by enantioselective enzymatic acylation of a racemic amine of formula (IV):

![Formula IV]

using a lipase (EC 3.1.1.3 in the international classification of enzymes),
with a carbonate of formula $R_1O$—(CO)—$OR_1$, wherein $R_1$ is as defined hereinbefore,
in an amount ranging from 1 to 15 molar equivalents relative to the amine of formula (IV),
in an organic or aqueous solvent, a mixture of organic solvents or a mixture of organic and aqueous solvents,
at a concentration from 5 to 500 g/L of compound of formula (IV) per liter of solvent or mixture of solvents,
at an Enzyme/Substrate ratio (E/S) of from 10/1 to 1/100, at a temperature from 25° C. to 40° C.

2. The process according to claim 1, wherein the lipase is selected from lipases of *Pseudomonas fluorescens*, of *Pseudomonas cepacia*, of porcine pancreas, and the lipases PS 'Amano' SD (*Burkholderia cepacia*) and IM (immobilized on Diatomite).

3. The process according to claim 2, wherein the lipase is a lipase of *Pseudomonas cepacia* or a lipase PS 'Amano' IM.

4. The process according to claim 1, wherein the E/S ratio is from 1/1 to 1/10.

5. The process according to claim 1, wherein the solvent is selected from TBME, THF, 2-MeTHF, 1,4-dioxane, and mixtures thereof, with a buffer of pH=7.

6. The process according to claim 1, wherein $R_1$ is an ethyl, allyl or benzyl group.

7. The process according to claim 1, further comprising reduction of the compound of formula (IX):

![Formula IX]

wherein $R_1$ represents a linear or branched $C_1$-$C_6$alkyl, allyl or benzyl group,
using a reducing agent selected from LiAlH$_4$ and Red-Al to yield a compound of formula (1):

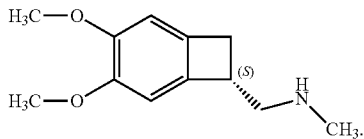

(I)

8. The process according to claim 7, wherein the compound of formula (I) subsequently is either coupled with a compound of formula (X):

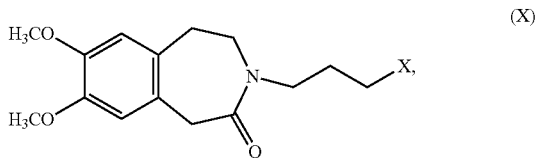

(X)

wherein X represents a halogen atom, or, in the presence of a reducing agent, subjected to a reductive amination reaction with a compound of formula (XI):

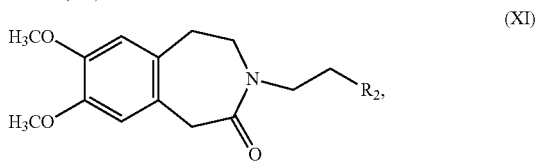

(XI)

wherein $R_2$ represents a group selected from CHO and $CHR_3R_4$, wherein $R_3$ and $R_4$ each represent a linear or branched $(C_1-C_6)$alkoxy group or, together with the carbon atom carrying them, form a 1,3-dioxane, 1,3-dioxolane or 1,3-dioxepane ring, to yield ivabradine, which is then converted into an addition salt with a pharmaceutically acceptable acid, in anhydrous or hydrate form.

9. The process according to claim 8, wherein X is an iodine atom.

10. The process according to claim 8, wherein the compound of formula (I) used in the reductive amination reaction is in the form of its hydrochloride salt, to yield ivabradine in the form of its hydrochloride salt.

11. The process according to claim 8, wherein the reductive amination reaction with a compound of formula (XI) is carried out in the presence of dihydrogen catalysed by palladium-on-carbon.

12. The process according to claim 10, wherein the reductive amination reaction with a compound of formula (XI) is carried out in the presence of dihydrogen catalysed by palladium-on-carbon.

* * * * *